(12) United States Patent
McConnell et al.

(10) Patent No.: US 7,524,309 B2
(45) Date of Patent: Apr. 28, 2009

(54) VARIABLE LENGTH FLEXIBLE CONDUIT FEEDER

(75) Inventors: Susan McConnell, Woodland Hills, CA (US); Lawrence C. Kiliszewski, Valencia, CA (US); Adam H. Molina, Valencia, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 671 days.

(21) Appl. No.: 10/033,993

(22) Filed: Dec. 28, 2001

(65) Prior Publication Data

US 2003/0122021 A1 Jul. 3, 2003

(51) Int. Cl.
*A61M 5/00* (2006.01)

(52) U.S. Cl. ...................................... 604/264

(58) Field of Classification Search ............ 137/255.16, 137/355.23, 355.12; 242/388.1, 405.1, 398, 242/241, 151; 604/93.01, 264, 66, 500, 502, 604/503, 164.01; 264/241
See application file for complete search history.

(56) References Cited

U.S. PATENT DOCUMENTS

| | | | | | |
|---|---|---|---|---|---|
| 3,835,854 | A | * | 9/1974 | Jewett ......................... | 604/159 |
| 4,200,249 | A | * | 4/1980 | Synstelien et al. ........ | 242/396.5 |
| 4,844,373 | A | * | 7/1989 | Fike, Sr. .................... | 242/588.1 |
| 5,236,143 | A | * | 8/1993 | Dragon ........................ | 242/377 |
| 5,392,808 | A | * | 2/1995 | Pierce .................... | 137/355.23 |
| 5,975,120 | A | * | 11/1999 | Novosel ................ | 137/355.23 |
| 5,984,224 | A | | 11/1999 | Yang | |
| 5,992,787 | A | | 11/1999 | Burke | |
| 6,327,507 | B1 | * | 12/2001 | Buchan ....................... | 607/115 |
| 6,554,218 | B2 | * | 4/2003 | Buyce et al. ............. | 242/388.6 |
| 6,589,229 | B1 | * | 7/2003 | Connelly et al. ......... | 604/890.1 |
| 2003/0098067 | A1 | * | 5/2003 | Peterson ................... | 137/355.2 |

FOREIGN PATENT DOCUMENTS

| | | |
|---|---|---|
| DE | 35 23 848 A1 | 1/1987 |
| DE | 101 06 74 | 6/2002 |
| DE | 101 06 074 A1 | 6/2002 |
| EP | 1 066 844 A1 | 1/2001 |
| EP | 1066844 | 1/2001 |
| EP | 1 157 712 A2 | 11/2001 |
| JP | 51-130089 | 11/1976 |
| JP | 06-75507 | 10/1994 |
| JP | 2000-060969 | 2/2000 |

(Continued)

OTHER PUBLICATIONS

Japanese Office Action for Application No. 2003-557396 filed Dec. 19, 2002.

*Primary Examiner*—Nicholas D Lucchesi
*Assistant Examiner*—Christopher D Koharski
(74) *Attorney, Agent, or Firm*—Gates & Cooper LLP

(57) ABSTRACT

Apparatuses and methods for dispensing flexible conduits, such as tubing or electrical cable, are disclosed, particularly for portable medical devices. An exemplary apparatus for dispensing flexible conduit or cable, includes a flexible conduit housing, including a base for temporarily housing a flexible conduit, the base having an opening for receiving the flexible conduit and a cover attached to the base for substantially closing the opening. The apparatus also includes an interface for mounting the housing. The flexible conduit is dispensable with the flexible conduit housing to a fixable variable length.

51 Claims, 5 Drawing Sheets

FOREIGN PATENT DOCUMENTS

| WO | 96/35472 | 11/1996 |
| WO | 99/41183 | 8/1999 |
| WO | WO 99/41183 | 8/1999 |
| WO | WO 00/56384 * | 9/2000 |
| WO | WO 02/46080 A1 | 6/2002 |

* cited by examiner

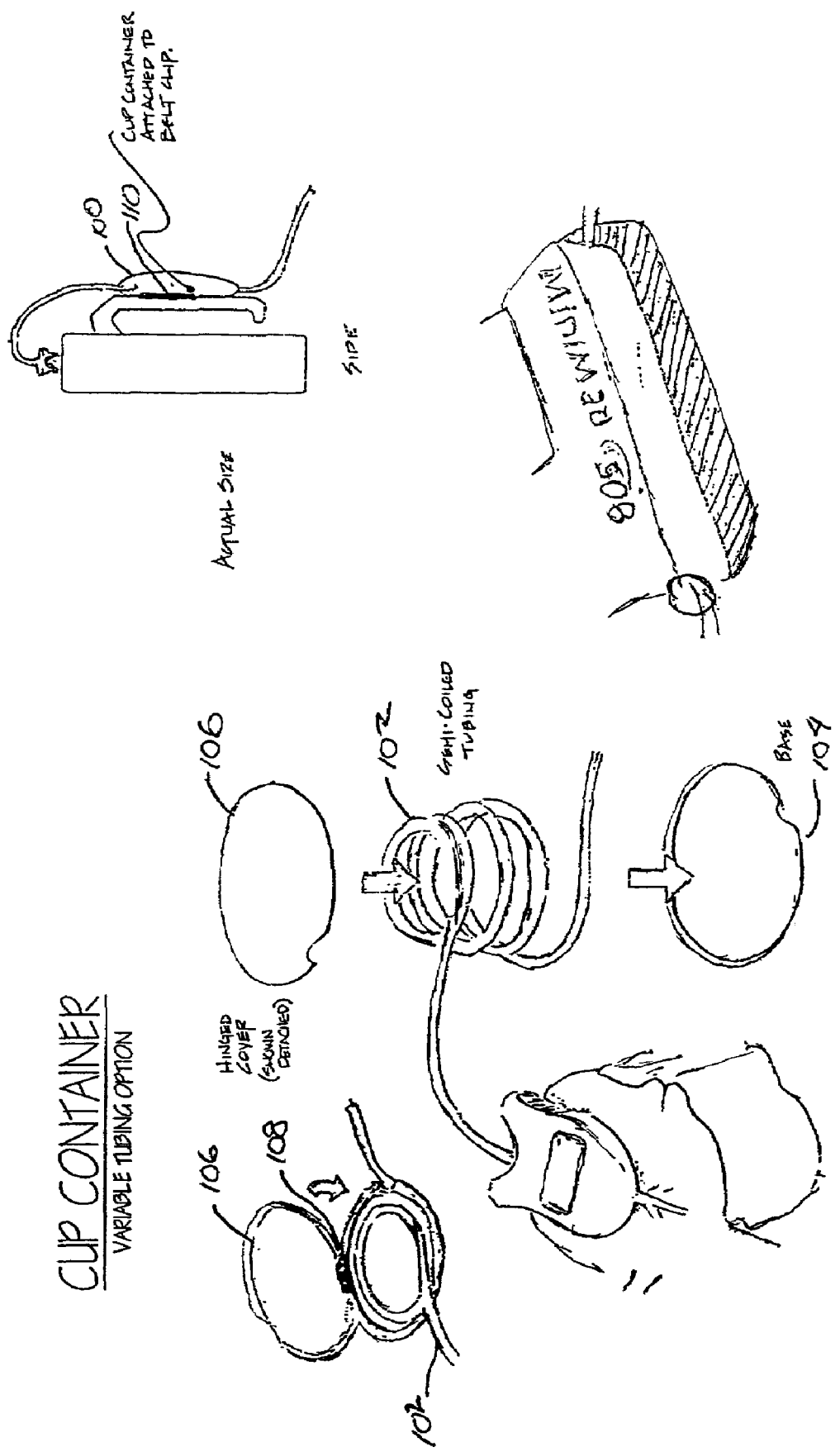

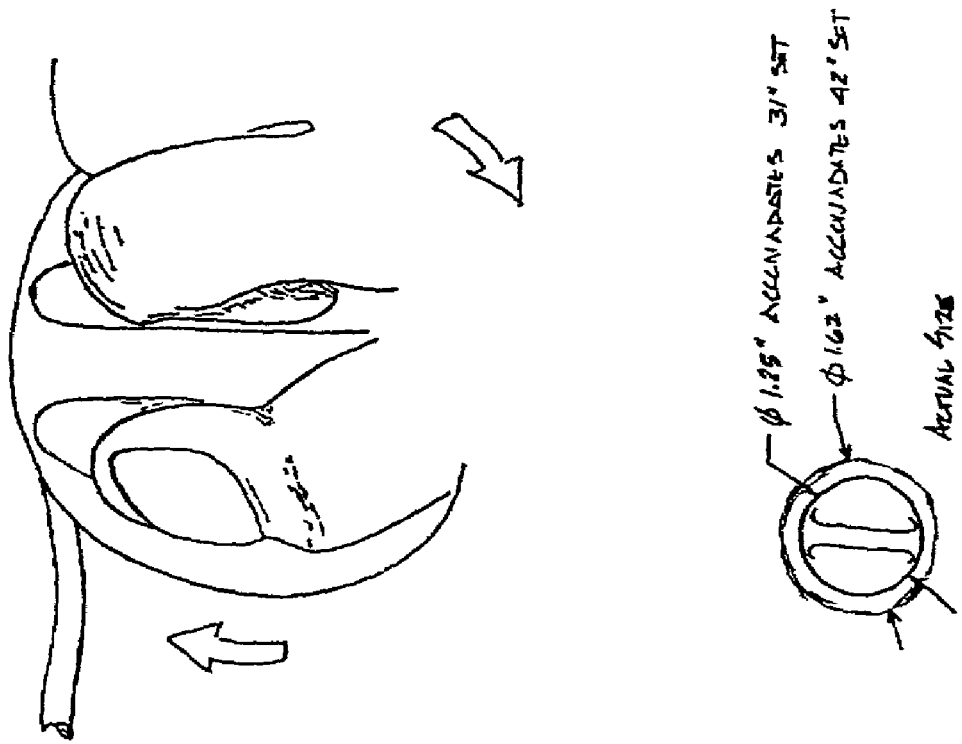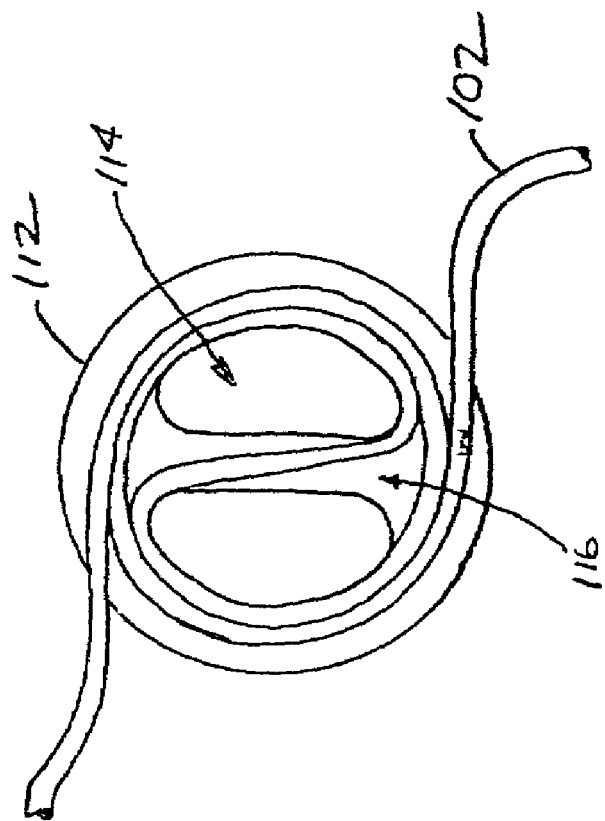
FIG. 2B

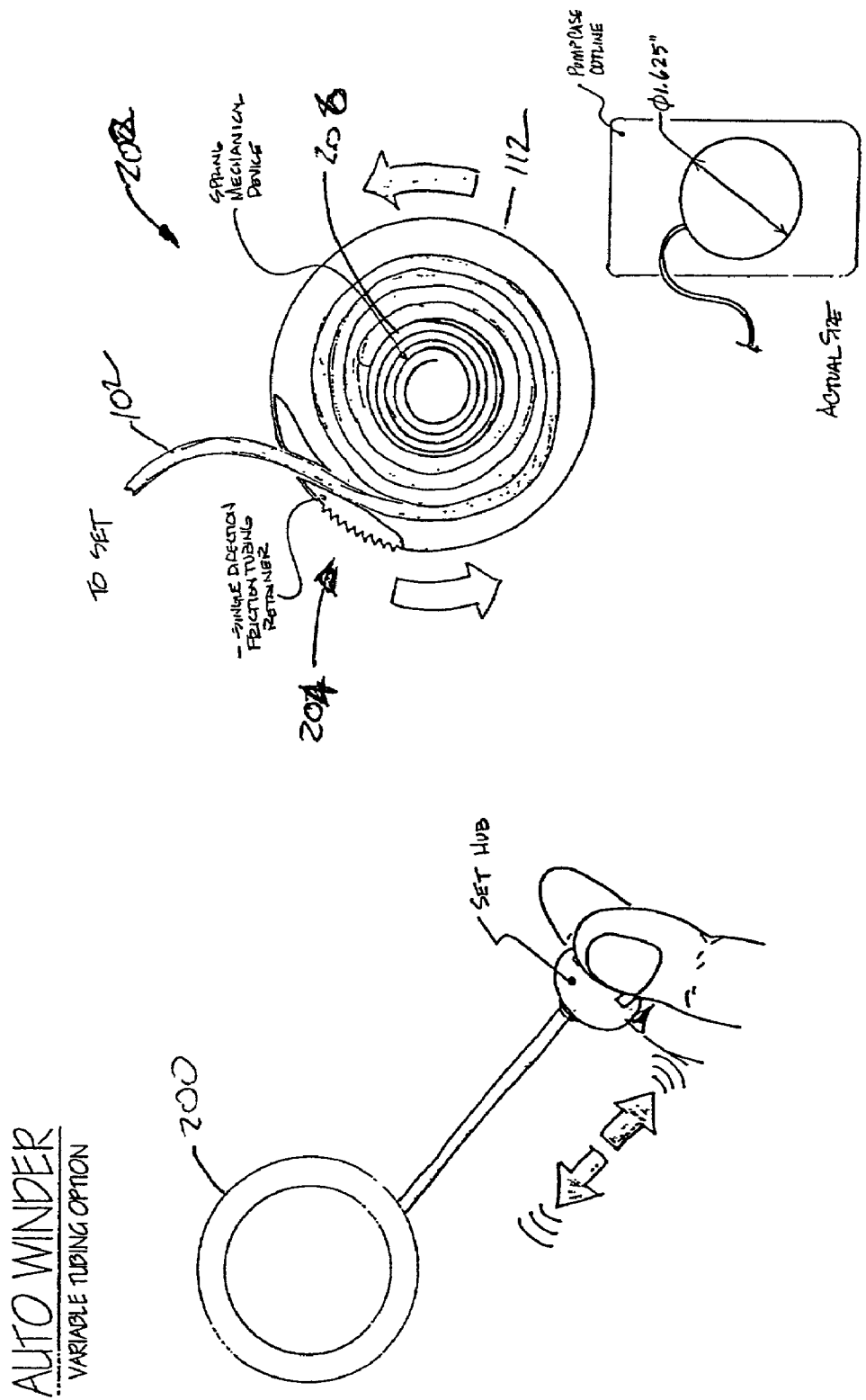

VARIABLE LENGTH FLEXIBLE CONDUIT FEEDER

BACKGROUND OF THE INVENTION

1. Field of the Invention

This invention relates generally to devices used in the delivery of medications. More specifically, this invention relates to devices which store and dispense conduits used with infusion devices and related devices.

2. Description of the Related Art

Infusion pump devices and systems and medication monitors are relatively well-known in the medical arts, for use in delivering or dispensing a prescribed medication such as insulin to a patient. In one form, such devices include a relatively compact pump housing adapted to receive a syringe or reservoir carrying a prescribed medication for administration to the patient through infusion tubing and an associated catheter. Medical monitors can take the form of a compact electrical device that is connectable via an electrical cable to a sensor that detects the presence of electrolytes, such as glucose.

The infusion pump can include a small drive motor connected via a lead screw assembly for motor-driven advancement of a reservoir piston to administer the medication to the user. Programmable controls are normally provided for operating the drive motor continuously or at periodic intervals to obtain a closely controlled and accurate delivery of the medication over an extended period of time. Such infusion pumps are utilized to administer insulin and other medications, with exemplary pump constructions being shown and described in U.S. Pat. Nos. 4,562,751; 4,678,408; 4,685,903; 5,080,653 and 5,097,122, which are all incorporated by reference herein.

The medical monitor works with small and flexible electrochemical sensors and can be used to obtain periodic readings over an extended period of time. In one form, flexible subcutaneous sensors are constructed in accordance with thin film mask techniques in which an elongated sensor includes thin film conductive elements encased between flexible insulative layers of polyimide sheets or similar material. Such thin film sensors typically include a plurality of exposed electrodes at one end for subcutaneous placement with a user's interstitial fluid, blood, or the like, and a corresponding exposed plurality of conductive contacts at another end for convenient external electrical connection with a suitable monitoring device through a wire or electrical cable. Typical thin film sensors are described in commonly assigned U.S. Pat. Nos. 5,390,671; 5,391,250; 5,482,473; and 5,586,553 which are incorporated by reference herein.

Infusion pumps and monitors of the general types described above have provided significant advantages and benefits with respect to accurate delivery of medication or other fluids over an extended period of time. The infusion pump or monitor can be designed to be compact as well as water resistant, and may thus be adapted to be carried by the user, for example, by means of a belt clip. As a result, important medication can be delivered to the user (or, in the case of a medical monitor, electrolytes measured) with precision and in an automated manner, without significant restriction on the user's mobility or life-style, including the ability to participate in water sports. The compact and portable nature of the pump or monitor affords a high degree of versatility in using the device. As a result, the ideal arrangement of the pump can vary widely, depending upon the user's size, activities, physical handicaps and/or personal preferences.

Infusion sets refer to the tubing (i.e. flexible conduit) and connection apparatus which provide a path for the medication to flow to the user from the reservoir or syringe located in the pump. The proper tubing length depends upon the desired pump arrangements. For any particular pump arrangement, infusion set tubing that is too long can be cumbersome for the user, while tubing that is too short can constrain the user's mobility. In addition, infusion sets must be periodically replaced to maintain proper hygiene.

In the case of compact medical monitors, the flexible conduit comprises an electrical cable that conveys electrical signals rather than a medication. Whether the flexible conduit is medical tubing (used with an infusion pump) or electrical cable (used with a medical monitor), the issues concerning constraining a user's mobility are very similar. Both infusion pumps and medical monitors are important in delivering medication to patients in a convenient and portable manner.

SUMMARY OF THE INVENTION

Embodiments of the present invention provide methods and apparatuses to facilitate the monitoring and treatment of physiological conditions through the use of variable length flexible conduit feeders. In some embodiments of the invention, the flexible conduit is medical tubing which is connectable to an infusion device of the type used to dispense fluids or medications such as insulin, or the like. In other embodiments of the invention, the flexible conduit is an electrical cable connectable to a medical sensor. In particular embodiments, the sensor is a glucose sensor of the type used by diabetics to facilitate the determination of an optimal insulin dose.

An exemplary embodiment of the invention includes a flexible conduit housing including a base for housing a flexible conduit, with the base having an opening for receiving the flexible conduit and a cover attached to the base for substantially closing the opening. With this apparatus, the flexible conduit can be dispensed from the flexible conduit housing to a fixable variable length. In preferred embodiments of the invention, the base and cover can be formed to make a clamshell flexible conduit housing. In a specific embodiment, the apparatus includes an interface for mounting the housing that is coupleable to a device (e.g. an infusion pump or other device) for dispensing a fluid through a tubing conduit. Typical interfaces include a clip, a strap, a clamp or a tape.

In another embodiment of the invention, the base is engageable to a replaceable cartridge for holding the flexible conduit. The replaceable cartridge can include a spool cartridge with the flexible conduit wound onto it. The replaceable cartridge can include a spool having a hub for engaging the flexible conduit at an adjustable position along a total length of the flexible conduit to adjust the fixable variable length. The flexible conduit can be wound onto the cartridge such that two ends of the flexible conduit can be dispensed simultaneously.

In another embodiment of the invention, the flexible conduit housing includes a spool for dispensing the flexible conduit to a fixable variable length. The spool in the housing can include a hub for engaging the flexible conduit at an adjustable position along a total length of the flexible conduit to adjust the fixable variable length. As with the cartridge, the flexible conduit can be wound onto the spool such that two ends of the flexible conduit can be dispensed simultaneously.

In yet another embodiment of the invention, a lockable spring driven winder is mounted within the flexible conduit housing for dispensing the flexible conduit to the fixable variable length. The spring driven winder can be lockable with a friction or a ratchet retainer.

Embodiments of the invention further provide a spool cartridge for holding a flexible conduit for use in a conduit dispenser housing. The spool cartridge holds the flexible conduit and includes a coupler for engaging a flexible conduit housing where the flexible conduit housing dispenses the flexible conduit to a fixable variable length.

In one embodiment, the flexible conduit is wound on the spool cartridge and two ends of the flexible conduit are dispensed simultaneously. The spool cartridge can further include a hub for engaging the flexible conduit at an adjustable position along a total length of the flexible conduit to adjust the fixable variable length.

In another embodiment, the spool cartridge can include a lockable spring driven winder for dispensing the flexible conduit to the fixable variable length. The spring driven winder can be lockable with a friction or a ratchet retainer.

BRIEF DESCRIPTION OF THE DRAWINGS

Referring now to the drawings in which like reference numbers represent corresponding parts throughout:

FIG. 1A illustrates an exemplary embodiment of a flexible conduit dispenser of the invention;

FIG. 1B illustrates an exemplary spool of the invention;

FIG. 2 illustrates an exemplary auto winder of the invention;

DETAILED DESCRIPTION OF THE PREFERRED EMBODIMENT

Figure 3:
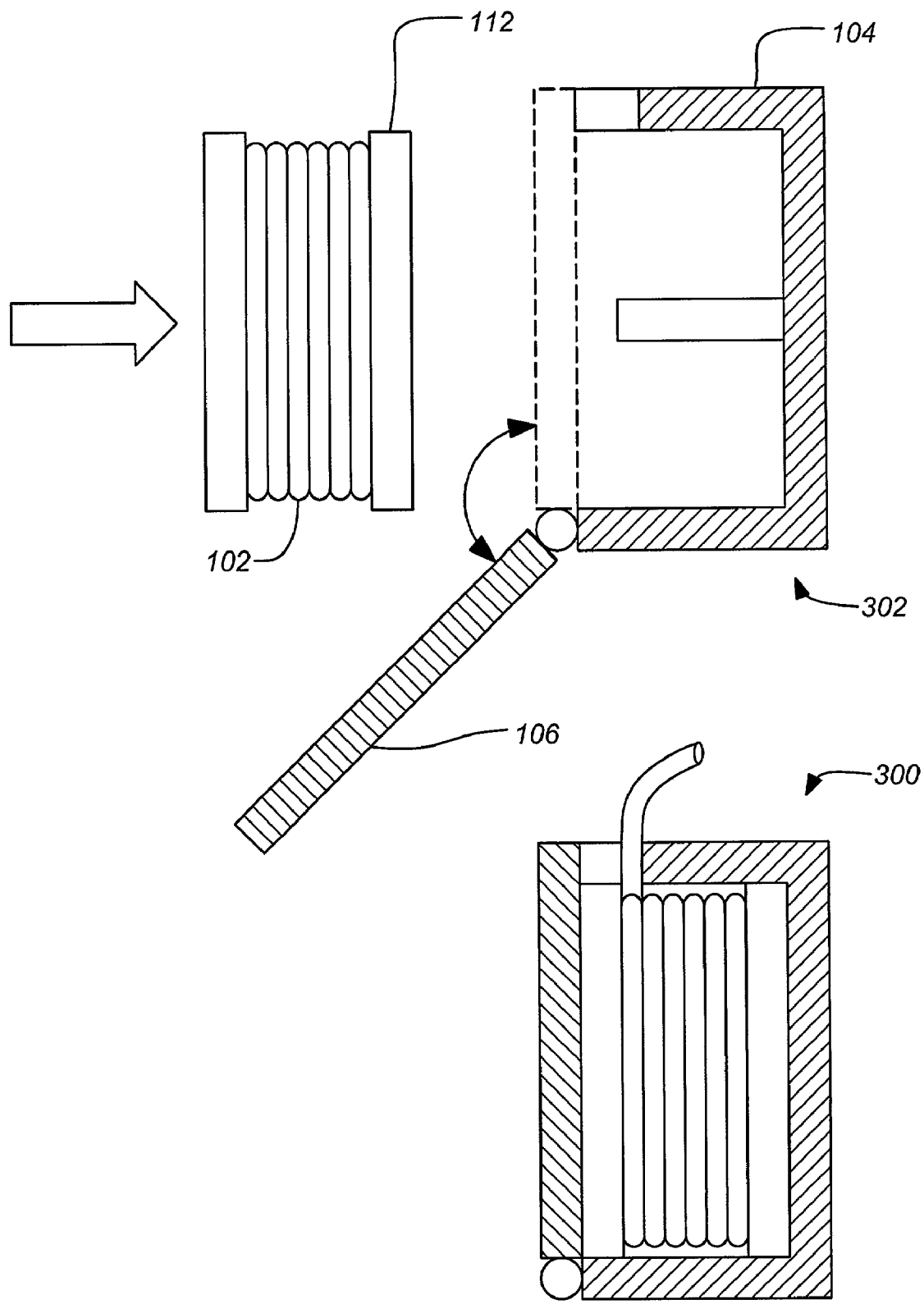
FIG. 3 illustrates an exemplary embodiment of a cartridge loaded flexible conduit dispenser of the invention.

In the following description, reference is made to the accompanying drawings which form a part hereof and which illustrate embodiments of the present invention. It is understood that other embodiments may be utilized and structural and operational changes may be made without departing from the scope of the present invention.

1. Overview

Embodiments of the invention described herein are directed to devices and methods for conveniently dispensing a flexible conduit, such as a medical tubing used to dispense medication from an infusion device (such as a pump, disposable device, or the like) or an electrical cable used with a medical monitor that receives a signal from a sensor. In these contexts, such embodiments of the invention are used to assist in dispensing fluids, such as, but not limited to, a medication, drugs, vitamins, hormones, saline, proteins, peptides, insulin, or the like, and the sensor may monitor various conditions, such as, but not limited to glucose, oxygen, drug or medication levels, temperature, pressure, heart rate, brain rate, or the like. Embodiments of the invention generally include a housing to contain the flexible conduit such that a dispensed length of the conduit can be varied according to the desire of a user. Such embodiments are particularly well suited for convenient and portable use and can be easily carried on the body of the user. Some embodiments utilize a replaceable flexible conduit cartridge that is used with the conduit dispenser.

Typical embodiments of the invention include a flexible conduit feeder that dispenses medical tubing, with a first end of the medical tubing being connected to an insulin infusion device and a second end of the medical tubing being connected to a device such as a needle, catheter, or the like, that is used to introduce insulin (and/or and insulin related peptides, insulin sensitizers or the like) into the body. Other typical embodiments of the invention include a flexible conduit feeder which dispenses electrical cable, with a first end of the electrical cable being connected to a glucose sensor and a second end of the electrical cable being connected to a device that provides an indication of the glucose sensor reading (e.g. a monitor) so that an optimal dosage of insulin (and/or and insulin related peptides, insulin sensitizers, or the like) can be determined. These embodiments of the invention provide for an increased flexibility in the use of such conduits and in this way facilitate medication delivery and/or sensor reading.

In embodiments of the invention designed for use with an infusion pump, the flexible conduit can be a medical tubing such as any one of the wide variety of medical tubings known in the art. Those in the art understand that tubing used in medical devices requires certain characteristics not shared by all tubing in general and that the tubing feeders described herein are designed for use with such medical tubing. For example, the tubing should be made from materials that are non-toxic, be resistant to rigors of sterilization and otherwise suitable for medical applications. The medical tubing can be of various lengths and dimensions, depending upon the site at which the medication is introduced into the body, the site at which the infusion pump is conveniently placed, as well as the medication and delivery rates required for each specific application. In such contexts, the tubing is adequately flexible to be coiled and yet sufficiently stiff to resist occlusions.

In embodiments of the invention designed for use with a medical sensor monitor, the flexible conduit can be an electrical cable that connects the monitor to a sensor of a sensor set. The electrical cable can include multiple conductors and should be designed with sufficient flexibility and shielding and insulation to convey noise-free signals to the medical sensor monitor. An exemplary electrical cable if found in U.S. patent application Ser. No. 09/511,819, filed Feb. 24, 2000, entitled "TEST PLUG AND CABLE FOR A GLUCOSE MONITOR", which is incorporated by reference herein.

2. Example Flexible Conduit Dispenser

FIG. 1A illustrates a first exemplary embodiment of a flexible conduit dispenser 100 of the invention. In this embodiment, flexible conduit 102 is precoiled into a base 104 of a housing. The base 104 is shaped as a low profile container with an opening to receive the flexible conduit 102. A cover 106 for the housing is used to close the opening when the device is in use. The cover 106 can be attached to the base 104 through one or more means such as a hinge 108 so that the cover 106 can be opened and closed over the opening. Alternate or additional attaching methods include a clip, a pin, a linkage, a flexible band, cord, mechanical fasteners, bonding material, or the like. The cover can be completely separable and attached with a snap fit or linked (e.g. as with a hinge or cord) to prevent its loss. In addition, the base 104 and cover 106 can be produced as an integral unit, such as by injection molding, where the hinge 108 is a flexible portion of the molded piece joining the base 104 and cover 106. In preferred embodiments, materials for all components of the device should be compatible for use with the desired medical device. However, if the materials do not contact the medication, the user or require sterilization, other materials may be used.

The base 104 and cover 106 can form a compact container, such as in the form of a clamshell. The flexible conduit 102 can be dispensed through small openings in the base 104 and/or cover 106. The user can open the cover 106, extract an appropriate length of flexible conduit 102 and re-close the cover 106 with the flexible conduit extending through the small openings. Alternatively, the user can pull free ends of the flexible conduit 102 directly through the small openings in the base 104 without opening the covet 106. The flexible conduit can then be used in conjunction with a device such as an infusion pump 2 to deliver medication to a user through an infusion set 4. The extracted length of flexible conduit 102 can be varied depending upon the desired arrangement of the infusion device and size of the user. Thus, a variable length of flexible conduit 102 is dispensed.

To further enhance use of the flexible conduit 102 dispenser, the dispenser 100 includes an interface 110 to attach the device in a location convenient or comfortable for the user. In this way, the dispenser 100 can be free floating and easily located (and relocated) in any position conducive to facilitate medication delivery or sensor reading. The interface 110 can be positioned on either the base 104 or covet 106. Various forms of the interface 110 are possible. For example, the interface 110 can be a tape, such as a two-sided tape, that can be used to attach the dispenser 100 to an infusion pump or monitor, or the skin of the user. Further, in other embodiments, the dispenser can be designed integral to a part, such as a clip, of the device. Alternatively, the interface 110 can include a clip so that the dispenser 100 can be temporarily attached to material or a belt.

In addition to a clamshell configuration, the base 104 and cover 106 can be made into a variety of shapes. Ideally, however, the cavity for holding the flexible conduit 102 is substantially round to provide for smooth extraction and replacement of the flexible conduit as the length is adjusted. In addition, the cavity can have a lip to prevent the flexible conduit 102 from slipping out of the opening inappropriately. Alternatively, the device can include a winder or spool element to aid in dispensing the flexible conduit.

FIG. 1B illustrates an exemplary spool 112 of the invention. The exemplary spool 112 includes a hub portion 114 that is used to anchor the flexible conduit 102 as it is wound onto the spool 112. In one embodiment, the hub portion 114 can include a passage 116 through which the flexible conduit 102 is directed. The passage 116 can operate to anchor the flexible conduit 102 as it is wound on the spool 112. When used in the dispenser 100, the flexible conduit 102 is dispensed and retracted simultaneously from both ends through openings (e.g. in the base 104). The openings can be located on a radial surface around the perimeter of the base. Although the openings can be in any configuration, positioning them on opposite sides of the base can provide more convenient use by maximizing the separation between the inlet and outlet ends of the flexible conduit 102.

In addition, the passage 116 can be used to adjust the dispensed length of flexible conduit 102 by sliding the flexible conduit 102 through the passage to a desired position before winding it onto the spool to vary the lengths on either side of the device. In one embodiment, the passage 116 can be formed between "half moon" shapes that appear as two pockets 118 from the opposite side of the spool 116. In this efficient configuration, the pockets 118 are used to grasp the spool and wind or unwind the flexible conduit 102. The passage 116 and spool 112 can be closed off (not shown) to prevent the flexible conduit 102 from falling off the hub 114 as the spool 112 is operated.

The spool 112 can be integrated with the base 104 by being constructed to have a round perimeter that is captured within the round opening of the base 104. Alternatively, the spool 112 can be fixed to the base 104 by a pin or axle or other methods, which allow it to rotate within the cavity. In one embodiment, the spool 112 is used as a cartridge that the user employs to periodically replace the flexible conduit 102.

FIG. 2 illustrates an exemplary embodiment of the invention having a spring driven winder or auto winder. In this embodiment, the spool 112 and housing 200 (e.g. including a base and cover) having an auto-winding device 202 that includes a retainer 204 and a spring 206. The spring 206 is applies a torque between the housing 200 and the spool 112 to draw the flexible conduit 102 into the housing 200, winding it onto the spool 112. The retainer 204 can be engaged to fix the dispensed length of flexible conduit 102 at any desired point.

The retainer 204 can be a friction retainer that operates between the housing 200 and the flexible conduit 102. In this embodiment, the pressure applied by the retainer 204 against the flexible conduit 102 must develop sufficient force to overcome the retraction torque of the spring 206. A balance must be struck so that the necessary pressure does not generate an occlusion in the flexible conduit 102 as it is used to deliver medication to a patient or electrical signals from a sensor.

In one embodiment of the invention, the retainer 204 operates against the spool 112 (e.g. against the rim or exterior surface of the spool) to avoid the potential for occlusions. In addition, the spool 112 presents more predictable surface properties for a friction retainer because it remains within the housing 200 during operation, limiting the potential for contamination that may cause a friction retainer to slip. Operating against the spool 112 also enables a variety of sizes of flexible conduit 102 to be used with the same housing without requiring adjustment to the friction retainer.

In another embodiment of the invention, the retainer 204 can be a ratchet retainer or pawl that operates between the housing and the spool 112. In such embodiments, the spool 112 includes ratchet teeth that are engaged by the retainer 204 when it is placed in the locked position. The ratchet retainer can be spring loaded against the ratchet teeth of the spool, such as with a torsion or cantilever spring. The flexible conduit 102 can be drawn out of the spool 112 and the retainer 204 will ratchet over the ratchet teeth, but it will not retract when released unless the retainer 204 is held open by the user. The retainer 204 can include a lock to secure it in a closed position so that the dispensed length of flexible conduit 102 can be temporarily fixed. Alternatively, the retainer 204 can be designed so that it is necessary to hold it open both to draw out or retract the flexible conduit 102. In this way, the retainer is "self-locking". The ratchet and pawl engagement of these embodiments provides all the advantages of the retainer 204 against the spool 112 discussed above with improved retention force due to the positive engagement of the pawl with the ratchet teeth.

In other embodiments, the retainer 204 (of the various forms described) can be used with a manual operating spooling, without a spring driven winder. In this case, the user can fix the length of dispensed flexible conduit 102. The retainer 204 can also be implemented as a feature of the base 104 and/or cover 106 such that closing the cover 106 effects fixing the dispensed length of flexible conduit 102.

3. Example Cartridge Loaded Flexible Conduit Dispenser

FIG. 3 illustrates an exemplary embodiment of a cartridge loaded flexible conduit dispenser 300 of the invention. As with the previous described embodiments, the present embodiment can include a dispenser housing 302 comprising a base 104 and cover 106. In this embodiment, the spool 112 includes a replaceable element so that new flexible conduit 102 can be conveniently supplied to the user. The elements of this embodiment (base 104, cover 106, spool 112, etc.) can possess any of the features described with the previous embodiments.

In this embodiment, the spool 112 includes a replaceable flexible conduit cartridge as shown in FIG. 3. The spool 112 includes a coupler, such as hole in the hub portion 114, which temporarily engages second coupler, such as an axle or pin of the housing 302. The axle can include a snap fitting on the end or other methods to positively retain or lock the spool 112 after it is installed in the housing 302. Alternatively, the spool 112 can be retained within the housing without an axle; where the round shape of the opening in the housing 302 serves to guide the rotation of the spool as the flexible conduit is dispensed. In such embodiments, the coupler can be a lip around the opening in the base 104. The spool 112 is thus snapped into the base 104 past the lip.

4. Example Method of Dispensing Flexible Conduit

Figure 4A:
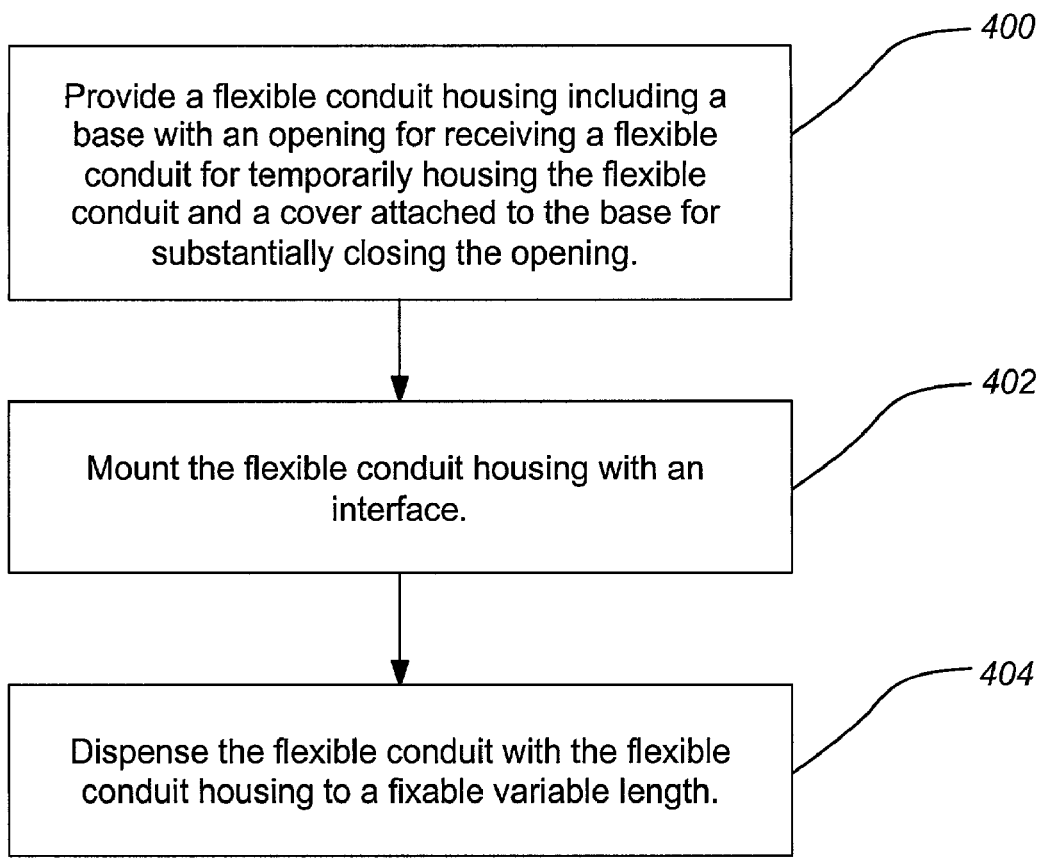
FIGS. 4A and 4B are flowcharts of exemplary methods of dispensing flexible conduit.
Figure 4B:
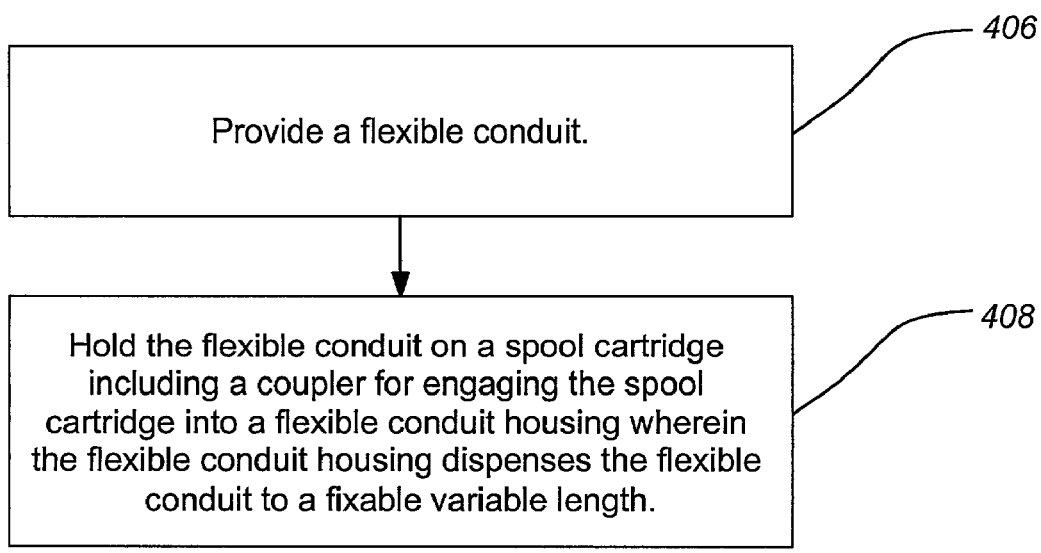

FIGS. 4A and 4B are flowcharts of exemplary methods of dispensing flexible conduit. FIG. 4A outlines a method of dispensing flexible conduit from a housing. At block 400, a flexible conduit housing is provided including a base with an opening for receiving a flexible conduit for temporarily housing the flexible conduit and a cover attached to the base for substantially closing the opening. At block 402, an interface is used to mount the flexible conduit housing. Finally at block 404, the flexible conduit is dispensed with the flexible conduit housing to a fixable variable length. The flexible conduit can be received on a spool, such as a replaceable spool cartridge that can include a hub with a passage for a simultaneous two ended dispensation of the flexible conduit. The spool can be spring loaded and dispensing the flexible conduit can entail operation of a retainer.

FIG. 4B outlines a method of dispensing flexible conduit using a spool cartridge. A flexible conduit is provided at block 406. At block 408, the flexible conduit is held on a spool cartridge including a coupler for engaging the spool cartridge into a flexible conduit housing. The flexible conduit housing dispenses the flexible conduit to a fixable variable length. The spool cartridge can include a hub with a passage for simultaneous two-ended dispensing of the flexible conduit.

5. Conclusion

It is intended that the scope of the invention be limited not by this detailed description, but rather by the claims appended hereto. The above specification and examples provide a description of the manufacture and use of the apparatus and method of the invention. Since many embodiments of the invention can be made without departing from the scope of the invention, the invention resides in the claims hereinafter appended.

What is claimed is:

1. An apparatus for dispensing medical infusion tubing used to deliver a fluid and treat a physiological condition, the apparatus comprising:
    a housing including:
        medical infusion tubing having a fitting adapted to connect to an infusion device and tubing dimensions permitting the infusion of insulin in a fluid from the infusion device through the medical infusion tubing to an individual having the physiological condition, wherein the fitting is not for piercing an organ of the individual;
        a base for temporarily housing the medical infusion tubing, the base having an opening for receiving the medical infusion tubing; and
        a cover attached to the base for substantially closing the opening; and
        an interface for mounting the housing; and
        a tubing locking mechanism disposed on the exterior of the housing, wherein the tubing locking mechanism comprises a friction retainer element that allows a user to fix a dispensed length of the medical infusion tubing at a desired point so that the medical infusion tubing is dispensable from the housing to a fixable variable length; or
        a manual winding mechanism disposed on the exterior of the housing, wherein the manual winding mechanism comprises a grasping element having a surface that allows a user to grasp and manually wind or unwind the medical infusion tubing disposed within the housing.

2. The apparatus of claim 1, wherein the physiological condition is diabetes.

3. The apparatus of claim 1, further comprising an infusion device, and wherein the infusion device is connected to the flexible conduit to assist in dispensing a fluid.

4. The apparatus of claim 1, further including a replaceable cartridge for holding the flexible conduit that is engageable to the base.

5. The apparatus of claim 4, wherein the replaceable cartridge includes a spool cartridge and the flexible conduit is wound on the spool cartridge.

6. The apparatus of claim 4, wherein the replaceable cartridge includes a spool including a hub for engaging the flexible conduit at an adjustable position along a total length of the flexible conduit to adjust the fixable variable length.

7. The apparatus of claim 4, wherein the flexible conduit is simultaneously dispensable from the replaceable cartridge from two ends.

8. The apparatus of claim 1, wherein the flexible conduit housing further includes a spool for dispensing the flexible conduit to a fixable variable length.

9. The apparatus of claim 8, wherein the spool includes a hub for engaging the flexible conduit at an adjustable position along a total length of the flexible conduit to adjust the fixable variable length.

10. The apparatus of claim 8, wherein the spool includes a replaceable cartridge.

11. The apparatus of claim 8, wherein the two ends of the flexible conduit are simultaneously dispensable from the spool.

12. The apparatus of claim 1, wherein the tubing locking mechanism comprises a lockable spring driven winder mounted on the flexible conduit housing for dispensing the flexible conduit to the fixable variable length.

13. The apparatus of claim 12, wherein the spring driven winder is lockable with a friction retainer.

14. The apparatus of claim 12, wherein the spring driven winder is lockable with a ratchet retainer.

15. The apparatus of claim 12, wherein the two ends of the flexible conduit are simultaneously dispensable from the lockable spring driven winder.

16. The apparatus of claim 1, wherein the base and cover form a clamshell flexible conduit housing.

17. The apparatus of claim 1, wherein the interface is coupleable to the infusion device.

18. The apparatus of claim 1, wherein the interface is selected from a group including a clip, a strap, a clamp and a tape.

19. An apparatus for storing medical infusion tubing used to deliver a fluid and treat a physiological condition, the apparatus comprising:
    a housing;

medical infusion tubing having a fitting adapted to connect to an infusion device and tubing dimensions permitting the infusion of insulin in a fluid from the infusion device through the medical infusion tubing to an individual having the physiological condition, wherein the fitting is not for piercing an organ of the individual; and a spool cartridge for holding the medical infusion tubing including a coupler for engaging the spool cartridge into the housing; and a tubing locking mechanism disposed on the exterior of the housing, wherein the tubing locking mechanism comprises a friction retainer element that allows a user to fix a dispensed length of the medical infusion tubing at a desired point so that the housing dispenses the medical infusion tubing to a fixable variable length; or a manual winding mechanism disposed on the exterior of the housing, wherein the manual winding mechanism comprises a grasping element having a surface that allows a user to grasp and manually wind or unwind the medical infusion tubing disposed within the housing.

20. The apparatus of claim 19, wherein the physiological condition is diabetes.

21. The apparatus of claim 19, wherein the flexible conduit is wound on the spool cartridge and two ends of the flexible conduit are simultaneously dispensable.

22. The apparatus of claim 19, wherein the spool cartridge includes a hub with a passage for engaging the flexible conduit at an adjustable position along a total length of the flexible conduit to adjust the fixable variable length.

23. The apparatus of claim 19, wherein the tubing locking mechanism comprises a lockable spring driven winder for dispensing the flexible conduit to the fixable variable length.

24. The apparatus of claim 23, wherein the spring driven winder is lockable with a friction retainer.

25. The apparatus of claim 23, wherein the spring driven winder is lockable with a ratchet retainer.

26. A method of dispensing medical infusion tubing to assist in dispensing a fluid to treat a physiological condition, the method comprising the steps of:

providing a housing including:

a base for temporarily housing medical infusion tubing, the base having an opening for receiving the medical infusion tubing;

medical infusion tubing having a fitting adapted to connect to an infusion device and tubing dimensions permitting the infusion of insulin in a fluid from the infusion device through the medical infusion tubing to an individual having the physiological condition, wherein the fitting is not for piercing an organ of the individual; and a cover attached to the base for substantially closing the opening; and a tubing locking mechanism disposed on the exterior of the housing, wherein the tubing locking mechanism comprises a friction retainer element that allows a user to fix a dispensed length of the medical infusion tubing at a desired point; or a manual winding mechanism disposed on the exterior of the housing, wherein the manual winding mechanism comprises a grasping element having a surface that allows a user to grasp and manually wind or unwind the medical infusion tubing disposed within the housing;

mounting the housing with an interface; and dispensing the medical infusion tubing from the housing to a fixable variable length.

27. The method of claim 26, wherein the fluid comprises insulin.

28. The method of claim 26, further comprising providing an infusion device; and connecting the flexible conduit to the infusion device to assist in dispensing a fluid.

29. The method of claim 26, further comprising providing a replaceable cartridge, and wherein the base is engageable to the replaceable cartridge for holding the flexible conduit.

30. The method of claim 29, wherein the replaceable cartridge includes a spool cartridge and the flexible conduit is wound on the spool cartridge.

31. The method of claim 29, wherein the replaceable cartridge includes a spool having a hub for engaging the flexible conduit at an adjustable position along a total length of the flexible conduit to adjust the fixable variable length.

32. The method of claim 29, wherein the flexible conduit is simultaneously dispensable from the replaceable cartridge from two ends.

33. The method of claim 26, wherein the flexible conduit housing further includes a spool for dispensing the flexible conduit to a fixable variable length.

34. The method of claim 33, wherein the spool includes a hub for engaging the flexible conduit at an adjustable position along a total length of the flexible conduit to adjust the fixable variable length.

35. The method of claim 33, wherein the spool includes a replaceable cartridge.

36. The method of claim 33, wherein the two ends of the flexible conduit are simultaneously dispensable from the spool.

37. The method of claim 26, wherein the tubing locking mechanism comprises a lockable spring driven winder mounted on the flexible conduit housing for dispensing the flexible conduit to the fixable variable length.

38. The method of claim 37, wherein the two ends of the flexible conduit are simultaneously dispensable from the lockable spring driven winder.

39. The method of claim 37, wherein the spring driven winder is lockable with a ratchet retainer.

40. The method of claim 37, wherein the spring driven winder is lockable with a friction retainer.

41. The method of claim 26, wherein the base and cover form a clamshell flexible conduit housing.

42. The method of claim 26, wherein the interface is coupleable to the infusion device for dispensing a fluid through the flexible conduit.

43. The method of claim 26, wherein the interface is selected from a group induding a clip, a strap, a clamp and a tape.

44. A method of storing medical infusion tubing to assist in dispensing a fluid to treat a physiological condition, the method comprising the steps of:

providing a housing comprising a tubing locking mechanism disposed on the exterior of the housing, wherein the tubing locking mechanism comprises a friction retainer element that allows a user to fix a dispensed length of the medical infusion tubing at a desired point; or a manual winding mechanism disposed on the exterior of the housing, wherein the manual winding mechanism comprises a grasping element having a surface that allows a user to grasp and manually wind or unwind the medical infusion tubing disposed within the housing;

providing medical infusion tubing having a fitting adapted to connect to an infusion device and tubing dimensions permitting the infusion of insulin in a fluid from the infusion device through the medical infusion tubing to an individual having the physiological condition, wherein the fitting is not for piercing an organ of the individual; and holding the medical infusion tubing on a spool cartridge including a coupler for engaging the spool cartridge into the housing, wherein the housing dispenses the medical infusion tubing to a fixable variable length.

45. The method of claim 44, wherein the fluid comprises insulin.

46. The method of claim 44, wherein the flexible conduit is wound on the spool cartridge and two ends of the flexible conduit are simultaneously dispensable.

47. The method of claim 44, wherein the spool cartridge includes a hub with a passage for engaging the flexible conduit at an adjustable position along a total length of the flexible conduit to adjust the fixable variable length.

48. The method of claim 44, wherein the tubing locking mechanism comprises a lockable spring driven winder for dispensing the flexible conduit to the fixable variable length.

49. The method of claim 48, wherein the spring driven winder is lockable with a friction retainer.

50. The method of claim 48, wherein the spring driven winder is lockable with a ratchet retainer.

51. An apparatus for dispensing medical infusion tubing used to deliver a fluid and treat a physiological condition, the apparatus comprising:

a housing including:
medical infusion tubing having a fitting adapted to connect to an infusion device and tubing dimensions permitting the infusion of insulin in a fluid from the infusion device through the medical infusion tubing to an individual having the physiological condition, wherein the fitting is not for piercing an organ of the individual;
a base for temporarily housing the medical infusion tubing, the base having an opening for receiving the medical infusion tubing; and
a cover attached to the base for substantially closing the opening;
an interface adapted to attach the apparatus to a user so that the apparatus is carried by the user, wherein the interface comprises a clip, a strap, a clamp, a tape or the like; and
a tubing locking mechanism disposed on the exterior of the housing, wherein the tubing locking mechanism comprises a friction retainer element that allows a user to fix a dispensed length of the medical infusion tubing at a desired point so that the medical infusion tubing is dispensable from the housing to a fixable variable length.

* * * * *